United States Patent [19]

Orelski

[11] 4,291,122

[45] Sep. 22, 1981

[54] BIOLOGICAL INDICATOR FOR STERILIZATION PROCESSES

[75] Inventor: Paula A. Orelski, Erie, Pa.

[73] Assignee: American Sterilizer Company, Erie, Pa.

[21] Appl. No.: 178,096

[22] Filed: Aug. 14, 1980

[51] Int. Cl.³ .............................................. C12Q 1/22
[52] U.S. Cl. ..................................... 435/31; 435/296
[58] Field of Search ................. 435/31, 296, 299, 300, 435/301, 805

[56] References Cited

U.S. PATENT DOCUMENTS

| | | | |
|---|---|---|---|
| 3,638,918 | 2/1972 | Denholtz | 206/222 |
| 3,661,717 | 5/1972 | Nelson | 435/31 |
| 3,791,930 | 2/1974 | Saxholm | 435/287 X |

Primary Examiner—Robert J. Warden
Attorney, Agent, or Firm—Robert D. Yeager

[57] ABSTRACT

A biochemical test system is disclosed for use in a biological fermentation sterilization indicator. The carbohydrate component of a nutrient broth media is removed from the media. The carbohydrate component may be disposed in the cavity of an encapsulated sealed glass ampul which contains a non-carbohydrated test solution. Microorganism spores are also disposed in the cavity. Upon completion of sterilization the ampul is broken; the contents mix. Fermentation of viable spores yields growth and color change and is a positive test (unsatisfactory sterilization); no fermentation yields no growth, no color change and satisfactory sterilization. The separation of carbohydrate prevents non-microorganism fermentation in the test reaction, and the appearance of a "false positive".

19 Claims, 1 Drawing Figure

U.S. Patent    Sep. 22, 1981    4,291,122
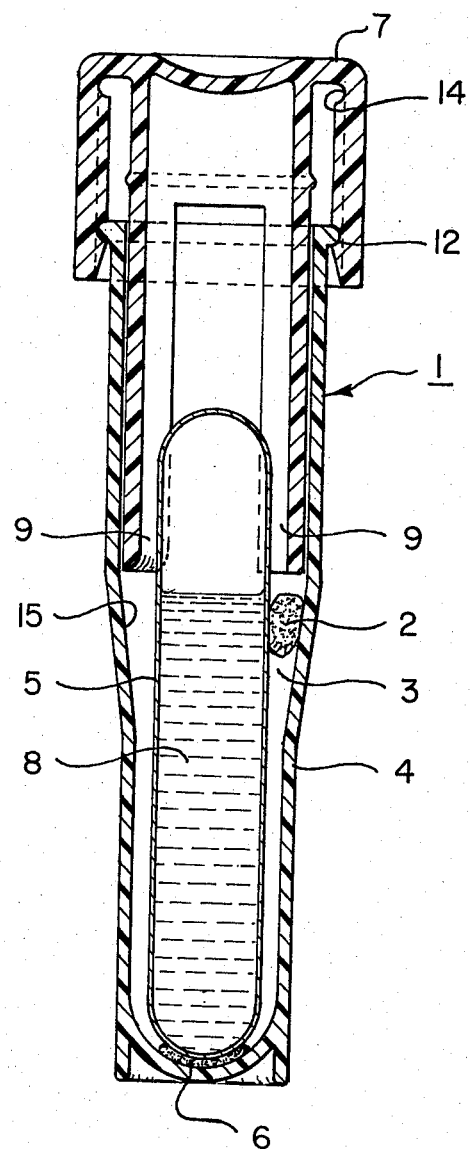

BIOLOGICAL INDICATOR FOR STERILIZATION PROCESSES

BACKGROUND OF THE INVENTION

1. Field of the Invention

This invention relates to mechanical test systems and more specifically to biological indicators for use in determining the effectiveness of gas or steam sterilization.

2. Description of the Prior Art

Chemical systems wherein components or reactants of the system are kept separate prior to initiating a specified indicating reaction upon mixing of the reactants are widely used, particularly in the health care industry, for various chemical, biochemical, or biological tests. In the latter area, which typically uses microorganisms as a testing medium, a nutrient growth media or component thereof is kept separate from the microorganism until the test is performed.

In fermentation tests, for example, as taught in U.S. Pat. No. 3,791,930, a solid media substrate, inoculated with a test strain of microorganisms, has sugar supported above the media substrate. When the sugar is moved onto the media substrate a characteristic fermentation reaction takes place.

In the case of biological fermentation indicators for use in steam or ethylene oxide sterilization, a nutrient broth is typically hermetically sealed in an encapsulated inner glass ampul and microorganism spores are disposed in the cavity of the surrounding enclosure. In a conventional biological indicator of this type, the spores are inoculated on a disc which is disposed in a transparent closed vial. The vial will have means for admitting the sterilant gas or steam, as for example a semipermeable membrane or an adjustable closure that admits steam or gas during the sterilization cycle. The vial will also contain encapsulated growth media such as sterile trypticase soy broth and glucose, and a pH indicator chemical, such as phenol red. These materials are encapsulated in a frangible ampul within the outer vial. The indicator is placed in a gas or ethylene oxide sterilization chamber along with the goods to be sterilized so that the spores within the indicator's vial are exposed to the sterilization along with, and in the same manner as, the goods being sterilized. Upon expected completion of sterilization the indicator is withdrawn from the chamber for testing. The inner frangible ampul is broken, releasing the media and pH chemical solution to mix with any microorganism spores that may have survived the sterilization. The vial is then incubated for a period of from five (5) to seven (7) days at temperatures of from 35 to 55 degrees Centigrade depending on the strain of spores used. If viable bacterial spores are present, their germination and growth will utilize the carbohydrate, glucose, that is in the growth media. Utilization of carbohydrate in the media produces acidic byproducts which lower the pH of the solution causing a visible color change in the pH indicator and thereby in the solution. No color change indicates no bacterial growth and a satisfactory sterilization. When phenol red is used as the pH indicator chemical, its initial red color becomes yellow in acid; yellow indicates the presence of viable bacteria and an unsatisfactory sterilization.

The spore bearing microorganism traditionally used for ethylene oxide sterilization is *Bacillus subtilis var. globigii; Bacillus stearothermophilus* is used in steam sterilization because of its greater resistance to moist heat.

The basic principle of the biological indicator is thus a fermentation of viable bacteriological spores which utilizes carbohydrate and produces an acid by-product. If, however, the carbohydrate content of the nutrient growth media is depleted by consumption by the microorganisms, the microorganisms will then begin to utilize the peptones in the nutrient broth. The byproducts of such metabolism, are alkaline and thus increase the pH of the broth thereby causing the color to revert to red with the appearance of a negative (no growth—no surviving bacteria) test result. This effect is very likely in indicators for ethylene oxide sterilization using *Bacillus subtilis,* which is known to be a weak carbohydrate ferment. Thus in formulating the nutrient broth for these indicators, an excess of carbohydrate had to be added to insure an accurate test result. However, when excess carbohydrates was used in the nutrient broth of indicators using *Bacillus stearothermophilus* in steam sterilization, the high temperatures and long periods of time of steam sterilization broke down the carbohydrate, forming an acid which lowered the pH. The phenol red, sensitive to this decrease, changed to an orange color, giving the appearance of what is termed in the art as a "false positive" (growth). Thus different indicators have been required for steam sterilization and ethylene oxide sterilization.

SUMMARY OF THE INVENTION

This invention permits the use of a biological indicator in either steam sterilization or ethylene oxide gas sterilization by the removal of the carbohydrate from the nutrient growth media. In the indicator of the present invention, the carbohydrate is releasably and discretely disposed apart from the other components of the indicator—the microorganism spores, the nutrient broth, and the pH chemical indicator. To conduct the sterilization test, the carbohydrate is released to mix with these other components to provide thereby the carbohydrate required for bacteria fermentation.

The carbohydrate preferably is disposed in dry, pellet or powder form in the outer vial of a vial-ampul type indicator; also contained in the outer vial are a bacteriological spore disc and a frangible ampul containing a (non-carbohydrated) nutrient broth media and pH indicator such as phenol red. Breaking of the inner ampul frees the liquid broth which solvates the carbohydrate and any surviving bacterial spores thereby releasing the carbohydrate for fermentation by the spores in the indicator solution.

The carbohydrate also may be disposed in a sealed compartment of the frangible ampul, separated from the nutrient broth media by an impermeable membrane, so that breaking of the ampul results in the release and bringing together of the indicator components.

BRIEF DESCRIPTION OF THE DRAWING

A longitudinal section of a biological indicator embodying the discrete carbohydrate of the present invention.

DESCRIPTION OF THE PREFERRED EMBODIMENTS

The discrete carbohydrate of the present invention is best embodied in the vial-ampul type biological fermentation indicator described in co-pending U.S. Application Ser. No. 153,136 filed May 27, 1980 entitled "Apparatus for Rupturing a Sealed, Frangible Container" and owned by the assignee of this application. The following detailed description will therefore discuss the carbohydrate in view of the structural features of this indicator. However, it will be appreciated by those skilled in the art that the discrete carbohydrate of the present invention may be utilized, within the spirit and scope of the invention, in biological fermentation indicators of varying structure.

Nutrient broth, such as trypticase soy broth, is a liquid media for the culture of microorganisms, which consists essentially of peptones, carbohydrate (particularly glucose), water and a phosphate buffer. A pH indicator chemical such as phenol red is also customarily placed in solution with the nutrient broth. Phenol red appears red in the (initial) solution of pH 7.3 and above (alkaline), and yellow at a pH of 7.0 and below (acid). The long exposure times to temperatures (about 121 degrees Centigrade) used in steam sterilization, which are considerably higher than those needed in ethylene oxide sterilization, break down the carbohydrate in the chemical system producing acids, and thereby lower the initial pH of 7.3 in the solution so that the solution appears orange in color. The color change produced in the solution by this breakdown of the carbohydrate is sufficiently ambiguous to lead an observer to conclude that the integrity of the chemical system has been destroyed. If the observer fails to notice the loss of integrity of the chemical system immediately after steam sterilization, the indicator is incubated at 55° C. It is here that the ambiguity of the orange color could indicate that viable microorganisms are present (false positive) and lead the observer to believe that the sterilization cycle was unsatisfactory.

By removing the carbohydrate from the broth, the integrity of the chemical system can be maintained.

In the biological indicator 1 of the present invention, shown in the FIGURE, the carbohydrate 2 is shown as a discrete component disposed in the cavity 3 of outer vial 4. Carbohydrate, disposed in this manner is still subject to the high temperatures of steam sterilization which had previously broken it down to acid by-products. However, the unexpected result of separating the carbohydrate from the peptones and other broth constituents, is an inhibition of carbohydrate degradation.

Carbohydrate 2 shown in the FIGURE, can conveniently be used in a solid state, such as a pellet or a disc of inert carrier material (e.g. paper) impregnated with the carbohydrate; it may also be coated on ampul 5 or be liquified in vial cavity 3. The carbohydrate may be discretely disposed in other states or forms within the spirit and scope of the invention.

In operation, carbohydrate 2, is disposed with sealed glass ampul 5 and microorganism spore disc 6 in vial cavity 3. Spore disc 6 is inoculated with a suitably resistant strain of microorganism spore such as *Bacillus stearothermophilus* (for steam). In ethylene oxide gas sterilization the spore strain of choice is *Bacillus subtilis*. Ampul 5 contains a sealed sterile test solution 8 consisting essentially of peptones, water and phosphate buffer. Also in test solution 8 is a pH indicator such as phenol red. Vial 4 engages cap 7 at a first locking engagement 12, and descending fins 9 of cap 7 cradle the upper portion of ampul 5. The cap and fin structure, not part of this invention, but discussed herein in the operation of the present invention, are more fully described in the aforesaid co-pending U.S. Application Ser. No. 153,136.

The indicator is placed in a sterile chamber with the load to be sterilized. In first locking engagement 12, the indicator will admit steam to the vial cavity 3 and thereby to the spore organisms on disc 6.

When the sterilization cycle is complete, the indicator is withdrawn and cap 7 is engaged in a second locking engagement 14, shown in the FIGURE, by pressure on the top of the cap. When cap 7 is thus pushed into the second engagement 14, vial 4 is sealed, and descending fins 9 move downwardly into vial cavity 3 to engage a taper 15 of the vial wall which forces fins 9 radially inward and crushes the glass ampul vial 5 so that test solution 8 flows into vial cavity 3 releasing carbohydrate 2 to mix with any viable spores on spore disc 6.

Thus a sealed and sterile system is produced for the fermentation of any viable spores present. If sterilization has been by steam, the indicator is incubated for seven days at 55 degrees Centigrade for observation of test results. A positive test is shown by a yellow color in the indicator indicating spore growth and an unsatisfactory sterilization, and a negative test is shown by a red color indicating no spore growth and a satisfactory sterilization. The procedure is the same for ethylene oxide sterilization with the exception of the temperature of incubation (37 degrees Centigrade) and the type of spore strain utilized.

The removal of carbohydrate from the broth has further ensured that the observed test result will be due to actual growth or non-growth of spores rather than independently produced chemical reactions of the indicator reagents.

What is claimed is:

1. A unitary sterilization indicator consisting of a transparent vial containing
   fermentable microorganism accessible to and subject to sterilization to substantially the equivalent degree as those objects being sterilized, and a carbohydrate in discrete solid dry form unavailable for metabolism by said microorganism prior to the dissolving of said carbohydrate; and
   an inner frangible ampul contained within the said vial and containing a liquid carbohydrate-free growth medium and pH color indicator, whereby upon completion of a sterilization cycle in which the said unitary indicator is contained within the sterilizer and removal of the indicator therefrom, the frangible ampul is broken and the said liquid medium and pH indicator are released into dissolving contact with the carbohydrate and the so-formed solution into contact with surviving said microorganism.

2. A method for monitoring the effectiveness of steam or gas sterilization which comprises the steps of
   (i) placing the unitary biological fermentation sterilization indicator of claim 1 within a sterilization chamber for a sterilization period,
   (ii) bringing said carbohydrate into dissolving contact with said so formed solution upon completion of said sterilization period and
   (iii) incubating said indicator for visible color change.

3. A unitary biological fermentation sterilization indicator containing a discrete carbohydrate releasably disposed within a transparent outer vial that further contains microorganism spores, and an inner frangible ampul containing a pH chemical indicator and carbohydrate-free growth media.

4. The indicator of claim 3 wherein said carbohydrate is disposed within a sealed frangible tube within said ampul.

5. The indicator of claim 3 where said carbohydrate is coated on the outer surface of said ampul.

6. The indicator of claim 3 wherein said carbohydrate is a powder disposed in said outer vial.

7. The indicator of claim 3 wherein said carbohydrate is a pellet disposed in said outer vial.

8. The indicator of claim 3 wherein said carbohydrate is disposed within a sealed compartment of said frangible ampul, out of contact with said pH indicator and growth media.

9. The indicator of claim 3 wherein said carbohydrate is a liquid disposed in said outer vial.

10. The indicator of claim 9 wherein said carbohydrate is further impregnated in an inert carrier material.

11. An improvement in a unitary biological fermentation sterilization indicator for use in a gas or steam sterilization chamber to monitor the effectiveness of gas or steam sterilization, said indicator having an outer vial containing microorganism spores accessible to gas or steam, an inner ampul containing a solution of carbohydrate-free nutrient broth and pH indicator, and means to release said solution to mix with said spores upon completion of sterilization, such that fermentation of viable spores in said solution, upon incubation, will produce visible color changes in said vial and absence of color change in said vial will indicate an effective sterilization; said improvement comprising;
a releasably disposed discrete carbohydrate.

12. The improved indicator of claim 11 wherein said carbohydrate is disposed in said outer vial.

13. The improved indicator of claim 12 wherein said carbohydrate is a powder.

14. The improved indicator of claim 12 wherein said carbohydrate is a pellet.

15. The improved indicator of claim 11 wherein said carbohydrate is a liquid.

16. The improved indicator of claim 15 wherein said carbohydrate is impregnated on an inert carrier material.

17. The improved indicator of claim 11 wherein said carbohydrate is disposed within a sealed tube within said inner ampul.

18. The improved indicator of claim 11 wherein said carbohydrate is coated on the outer surface of said inner ampul.

19. In a unitary biological-fermentation sterilization indicator consisting of a transparent vial containing a fermentative microorganism accessible to the sterilization medium when the vial is placed in a sterilizer, and a frangible ampul disposed within the said vial, the combination of a carbohydrate free liquid growth medium contained within the ampul and a discrete solid carbohydrate disposed within the vial outside of the ampul and unaccessible to the said microorganism.

* * * * *